US00PP33628P2

(12) United States Plant Patent
Hansen

(10) Patent No.: US PP33,628 P2
(45) Date of Patent: Nov. 9, 2021

(54) ***ASTER* PLANT NAMED 'PINK CRUSH'**

(50) Latin Name: *Symphyotrichum novae-angliae*
Varietal Denomination: Pink Crush

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,045

(22) Filed: Feb. 23, 2021

(51) Int. Cl.
*A01H 5/02* (2018.01)
*A01H 6/14* (2018.01)

(52) U.S. Cl.
USPC ..... Plt./355
CPC ..... *A01H 6/1408* (2018.05)

(58) Field of Classification Search
USPC ..... Plt./355
CPC ..... A01H 6/1408; A01H 5/02
See application file for complete search history.

*Primary Examiner* — Keith O. Robinson

(57) ABSTRACT

A new and distinct *Aster* plant named 'Pink Crush', with compact, heavily-branched, very rounded mound habit, dark green, lanceolate foliage and large, densely-packed, semi-double inflorescences with numerous, overlapping, rose-pink ray florets with no fading in color beginning in early fall and continuing for up to eight weeks. The new plant is useful for landscaping, as a specimen or en masse and as a cut flower or containers.

1 Drawing Sheet

Botanical designation: *Symphyotrichum novae-angliae*.
Cultivar denomination: 'Pink Crush'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 23, 2020. Prior to that, on Feb. 1, 2020 the claimed plant was displayed as a photograph with a brief non-enabling description on a website operated by Walters Gardens, Inc., followed by listing with a photograph and brief description in the Walters Gardens 19-20 Catalog circulated on May 20, 2020. Walters Gardens, Inc. obtained the plant and all information relating thereto, from the inventor. No plants of *Aster* 'Pink Crush' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct *Aster* herein also referred to as *Aster* 'Pink Crush', by the cultivar name, 'Pink Crush', or as the new plant. The new plant was selected by the inventor as a single seedling resulting from a self-pollination of a proprietary, unreleased, unnamed seedling known only by the breeder code 13-1-1 (not patented) in a research facility of a wholesale perennial grower based in Zeeland, Mich., USA. The cross was performed on Jul. 7, 2015 and the seeds from this cross were collected in the fall of 2015. The single seedling was then isolated and compared in subsequent years to other *Aster* and subsequently found to be different from all cultivars known to the discoverer and eventually given the breeder code 15-1-4.

Asexual propagation at the same nursery in Zeeland, Mich., USA by basal shoot tip cuttings and division since October of 2016 has shown 'Pink Crush' to be stable and reproduce true to type in successive generations.

SUMMARY OF THE PLANT

*Aster* 'Pink Crush' has not been observed in all possible environmental conditions. The phenotype may vary slightly with changes in environments such as light intensity, fertility, water availability, etc. without, however any variation in genotype.

*Aster* 'Pink Crush' is distinct from all cultivars known to the inventor in the following traits:

1. Compact, very rounded mound of about 29 cm tall and 42 cm wide;
2. Dark green lanceolate foliage;
3. Very stiff, heavily-branched peduncles with densely-packed inflorescences;
4. Inflorescences with multiple rows of overlapping rose-pink ray florets with no fading with maturity;
5. Long flowering period beginning early fall and continuing for about six weeks;

Plants of *Aster* 'Pink Crush' are most similar to 'Pink Dome' (not patented), 'Vibrant Dome' U.S. Plant Pat. No. 19,538 and 'Billowing Pink' U.S. Plant Pat. No. 32,556. 'Pink Dome' is larger in habit, both taller and broader than the new plant, and the more numerous ray florets are more pale-purple. 'Vibrant Dome' is closer in ray floret color, but has longer ray florets and fewer ray florets per inflorescence and the plant has fewer inflorescences when in full flower. 'Billowing Pink' has fewer and slightly shorter ray petals per inflorescence, is taller in habit, and the ray floret color is lighter purple with less red hue. 'X Blue' U.S. Plant Pat. No. 29,109 has slightly smaller and slightly fewer ray florets per inflorescence, and the ray florets are strong to light purple.

The parent plant, 13-1-1 has a taller and less compact habit and the ray florets were not as dark of a hue.

BRIEF DESCRIPTION OF THE DRAWINGS

The color drawings illustrate the overall characteristics of *Aster* 'Pink Crush' as a two-year-old plant in a full-sun trial garden in Zeeland, Mich. The colors are as true as reasonably possible given the technology available. The color values may vary slightly depending on light intensity and quality.

DETAILED BOTANICAL DESCRIPTION

Figure 1:
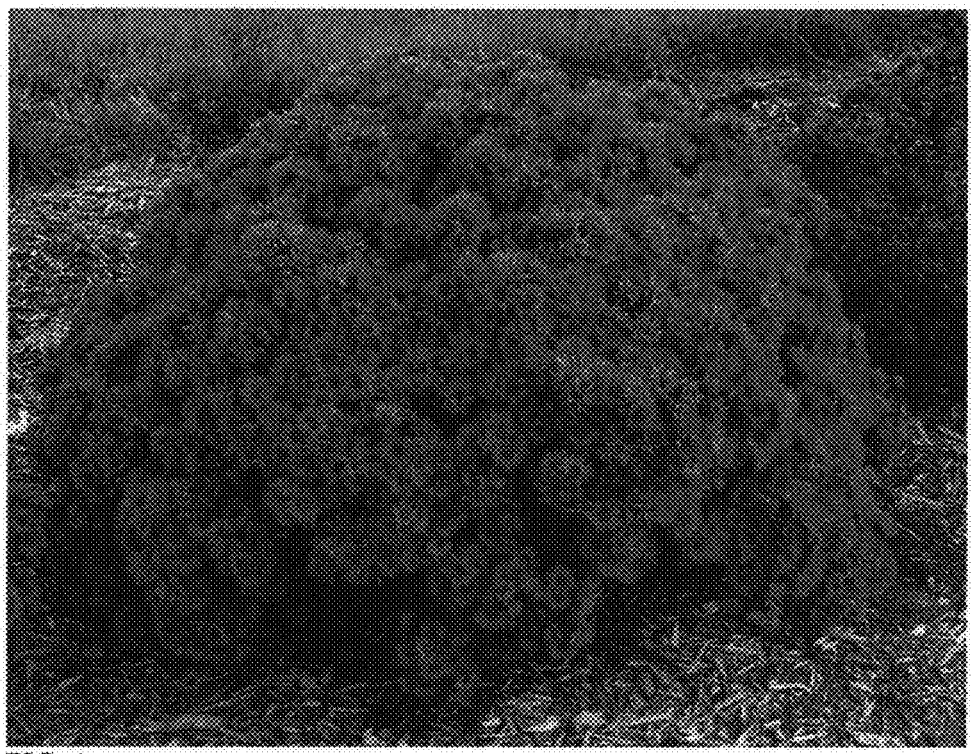
FIG. 1 shows the new plant in a trial facility.
Figure 2:
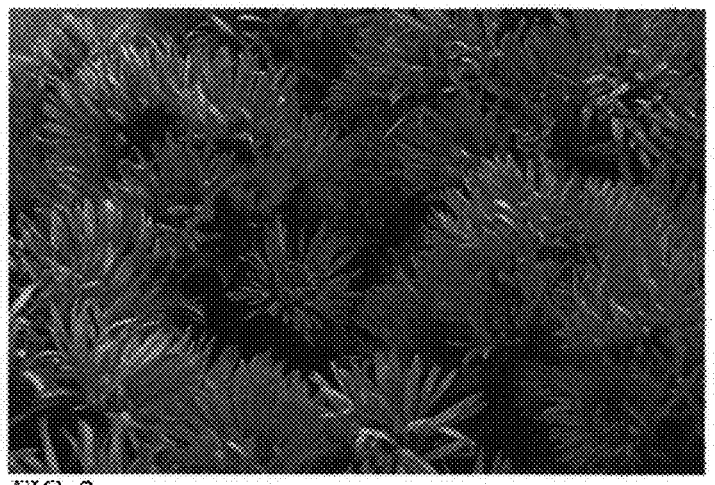
FIG. 2 shows a close-up of the inflorescences of the new plant.

The following description of the new plant is based on a one-year-old plant growing in a full-sun production field in Hamilton, Mich., USA. Except for ordinary dictionary color usage, color references are according to The Royal Horticultural Society Colour Chart, 2015 edition.

Parentage: Female or seed parent 13-1-1; male or pollen parent 13-1-1;

Asexual propagation: Basal shoot cuttings, about 10 to 14 days to initiate roots; time to finish as #1 field grown size about 6 months;

Plant habit: Herbaceous, winter-hardy, rhizomatous, perennial mound with stiff, upright, heavily-branched stems; up to 29.0 cm tall and 42.0 cm wide; average about 27.0 cm tall and about 40.0 cm across;

Leaves: Alternate; simple; lanceolate; acute apex; base truncate, clasping; margin entire, micro-ciliolate; adaxial glabrous and semi-lustrous abaxial micro-puberulent; up to about 5.0 cm long and about 1.6 cm wide; average size about 4.6 cm long and 1.3 cm wide;

Leaf color: Young expanding leaves adaxial distally nearest RHS 138A and proximally nearest RHS 145A, abaxial distally nearest RHS 138A and proximally nearest RHS 145A; mature leaves adaxial nearest RHS NN137B, abaxial between RHS 147B and RHS 147C;

Foliar fragrance: None noted;

Veins: Longitudinal reticulate; glabrous adaxial and puberulent abaxial;

Vein color: Adaxial RHS 146B on midrib, secondary nearest RHS NN137B; abaxial midrib and secondary nearest RHS 148C;

Petiole: Sessile;

Stems: Upright; cylindrical; micro-puberulent; stiff; heavily branched; approximately 10 per plant; to about 26 cm long and 0.5 cm diameter at base;

Stem color: Between RHS 138B and RHS 138C;

Branches: Cylindrical; micro-puberulent; up to 18 per main stem; in upper one-third and at base; to about 16.0 cm long and 0.3 cm diameter;

Branch color: Between RHS 138B and RHS 138C;

Inflorescence: Radiate capitulum; semi-double; composite consisting of about 120 to 160 ray florets and about 120 to 150 disk florets; on heavily branched terminal stems; individual inflorescence about 45.0 mm diameter, about 18.0 mm tall from bottom of involucral bracts to top of center disk tepals; disk portion about 10.0 mm across; attitude mostly upright; produced on branched stems with about 200 to 4600 inflorescences per plant and about 40 per stem;

Flower season: Starting in early fall and continuing for about eight weeks; Disk color: nearest RHS 192C;

Receptacle: About 6.0 mm tall and 8.0 mm across; color nearest RHS 148C;

Inflorescence fragrance: Not detected;

Phyllaries: About 80 in four whorls; linear; narrowly acute apex; truncate base; margin entire and micro-ciliate; outer or lower set about 13.5 mm long and 2.0 mm across, inner set about 10.0 mm long and 1.5 across; micro-puberulent adaxial and abaxial; held horizontally, not adpressed to ray florets;

Phyllary color: Adaxial nearest RHS 137A with strong overtone of nearest RHS 187A, abaxial nearest RHS 146A with a light blush of nearest RHS 187A;

Involucre: Oblate; consisting of about 80 strongly overlapping phyllaries or involucral bracts; about 8 mm long and 20 mm wide;

Flowering period: Late August for up to eight weeks depending on weather;

Inflorescence longevity: 10 to 14 days;

Inflorescence buds: With ray florets still erect 19.0 mm tall and 14.0 mm across; round, columnar;

Inflorescence bud color: Ray florets while still upright exposed abaxial petal color nearest RHS 72B; phyllaries color nearest RHS 146A with light blush of nearest RHS 187A;

Ray florets: Imperfect; pistillate; typically about 120 to 160 per inflorescence; held horizontal to about 30 degrees above horizontal when mature;

*Style*.—Cylindrical; about 7.0 mm long and about 0.2 mm diameter; color nearest RHS 70B.

*Stigma*.—Bifid, cylindrical; 2.0 mm long and 0.2 mm diameter; color nearest RHS N79A.

*Ovary*.—Inverted conical, acute base, truncate apex; about 1.0 mm long and 0.7 mm diameter in middle; color nearest RHS NN155C.

*Pappus*.—About 5.0 mm long; color nearest RHS 159D.

Ray floret ligule: Linear with basal claw; glabrous; acute apex; attenuate base; entire margin; flat, not twisted; size 19.0 mm long and 2.0 mm wide;

*Ligule color*.—When first open flat adaxial nearest RHS 72A and abaxial nearest RHS 72B; when mature adaxial nearest RHS 72A and abaxial nearest RHS 72B; base between RHS 145C and NN155D.

Disk florets: About 120 to 150 per capitulum; tubular; glabrous; consisting of five tepals, staminal tube and pistil; size about 10.0 mm long to exserted stigma by 1.0 mm wide at apex; angle upright;

*Corolla tube*.—Consisting of five linear fused tepals; about 5.0 mm long and 1.0 mm across at apex; fused in basal 4.5 mm; apex acute; margin entire.

*Tepal color*.—When first open adaxial and abaxial apices nearest RHS 178B, center and basal portion nearest RHS 145D; at maturity adaxial and abaxial apices nearest RHS 178B, center and basal portion nearest RHS 145D.

*Staminal tube*.—Made up of five connate stamens; about 2.0 mm long and 1.0 mm diameter; color between RHS 165B and RHS 165C.

*Filaments*.—About 2.0 mm long and about 0.1 mm diameter; color nearest RHS 155D.

*Pollen*.—Abundant; fine, round, closest to RHS 17B.

*Style*.—Bifid; cylindrical; exserted, longer than staminal tube at maturity; about 8.0 mm long and 0.2 mm diameter; color upon opening nearest RHS NN155C, upon maturity proximally nearest RHS NN155C and distally nearest RHS 185B.

*Stigma*.—Bifid; reflexing as it matures; about 2.0 mm long and 0.2 mm diameter; color nearest RHS 20A maturing to nearest RHS 185B.

*Ovary*.—Ellipsoidal; apex acute, base truncate; 1.0 mm long and 0.7 mm across; color nearest RHS NN155C.

Seed: Has not yet been observed;

*Aster* 'Pink Crush' resists lodging and is tolerant temperatures in USDA zones 3 through 8. It is not known to be tolerant of diseases and pest that are common to other *Aster* cultivars.

I claim:

1. A new and distinct cultivar of *Aster* plant named 'Pink Crush' as described and illustrated.

* * * * *